United States Patent
Gliner et al.

(10) Patent No.: US 11,986,422 B2
(45) Date of Patent: May 21, 2024

(54) VANE PUMP FOR MEDICAL INSTRUMENT

(71) Applicant: JOHNSON & JOHNSON SURGICAL VISION, INC., Santa Ana, CA (US)

(72) Inventors: Vadim Gliner, Haifa (IL); Ilya Sitnitsky, Nahariya (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 820 days.

(21) Appl. No.: 16/689,340

(22) Filed: Nov. 20, 2019

(65) Prior Publication Data

US 2021/0146019 A1  May 20, 2021

(51) Int. Cl.
*A61M 1/00* (2006.01)
*A61F 9/007* (2006.01)
*A61M 3/02* (2006.01)

(52) U.S. Cl.
CPC .......... *A61F 9/00736* (2013.01); *A61M 1/63* (2021.05); *A61M 1/77* (2021.05); *A61M 1/774* (2021.05); *A61M 3/0202* (2021.05); *A61M 2205/3334* (2013.01); *A61M 2210/0612* (2013.01)

(58) Field of Classification Search
CPC ........ F04C 15/06; F04C 2/344; F04C 2/3446; F04C 14/06; F04C 14/065; F01C 21/08; F01C 21/0809; F01C 21/089; A61M 1/0058; A61M 2210/0612; A61M 3/0258; A61M 3/022; A61M 1/77; A61M 5/14232; A61M 2205/3331; A61M 2205/3334; A61M 1/0062

USPC .......................................................... 604/43
See application file for complete search history.

(56) References Cited

U.S. PATENT DOCUMENTS

| | | | |
|---|---|---|---|
| 3,473,478 A * | 10/1969 | Little, Jr. | ............ F01C 21/0845 417/310 |
| 4,183,723 A | 1/1980 | Hansen | |
| 7,670,330 B2 | 3/2010 | Claus | |
| 7,967,777 B2 | 6/2011 | Edwards | |
| 8,011,909 B2 | 9/2011 | Dong | |
| 8,435,207 B2 | 5/2013 | Baker | |
| 9,522,221 B2 | 12/2016 | Muri | |
| 10,251,983 B2 | 4/2019 | Raney | |

(Continued)

*Primary Examiner* — Ariana Zimbouski
*Assistant Examiner* — Anna E Goldberg-Richmeier
(74) *Attorney, Agent, or Firm* — Johnson & Johnson Surgical Vision, Inc.

(57) ABSTRACT

A medical system includes a medical instrument including an irrigation and aspiration channel to carry irrigation fluid to, and remove aspirated matter from, a distal end of the medical instrument, a reservoir to store the irrigation fluid, a receptacle to collect the aspirated matter, and a vane pump including a pump housing having an inner surface around a pumping chamber, the pump housing including irrigation inlet and outlet ports coupled to the pumping chamber and respectively connected to the reservoir and the irrigation channel, and aspiration inlet and outlet ports coupled to the pumping chamber and respectively connected to the aspiration channel and the receptacle, and wherein the vane pump is configured to simultaneously pump via the pumping chamber, at substantially the same flow rate, the irrigation fluid from the reservoir to the distal end and the aspirated matter from the distal end to the receptacle.

12 Claims, 7 Drawing Sheets

(56) References Cited

U.S. PATENT DOCUMENTS

| | | | |
|---|---|---|---|
| 2008/0124237 A1* | 5/2008 | Viken | F04C 14/08 |
| | | | 418/142 |
| 2008/0125698 A1 | 5/2008 | Gerg et al. | |
| 2014/0074011 A1* | 3/2014 | Charles | A61F 9/00736 |
| | | | 210/252 |
| 2014/0163455 A1* | 6/2014 | Wilson | A61M 1/774 |
| | | | 604/28 |
| 2015/0104330 A1* | 4/2015 | Chin | F04B 43/10 |
| | | | 417/320 |

* cited by examiner

VANE PUMP FOR MEDICAL INSTRUMENT

FIELD OF THE INVENTION

The present invention relates to medical systems, and in particular, but not exclusively, to pumping fluid in medical systems.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Pressure may also be applied to increase the internal pressure within the eye. This lowers the chances of complications later in the surgery. Then a small incision is made in the cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates particles from the cataract through the tip. The pump is typically controlled with a microprocessor. The pump may be a peristaltic or a venturi type of pump. Aspirated fluids are replaced with irrigation of a balanced saline solution to maintain the anterior chamber of the eye. After removing the cataract with phacoemulsification, the softer outer lens cortex is removed with suction. An Intraocular Lens (IOL) is introduced with the phacoemulsification probe through its needle into the empty lens capsule and the IOL unfolds. Small struts may hold the IOL in place. Once correctly installed the IOL restores the patient's vision.

U.S. Pat. No. 8,435,207 to Baker, et al., describes irrigation and/or aspiration devices and methods that may be configured to aspirate and irrigate alone, sequentially, or concurrently. The devices and methods may provide a base with a removable head, and adapted for partial or complete separation of the irrigation and aspiration functions. The devices and methods can be configured to aspirate and/or irrigate the nasal and sinus cavities. The devices and methods may be manually and/or automatically controlled. The devices and methods may include removable, and/or replaceable, and/or refillable, and easily cleanable reservoirs for aspirant and irrigant. The device head and/or aspirant reservoir may comprise a diagnostic device, i.e., test device and/or container after use of the devices and methods.

U.S. Pat. No. 7,670,330 to Claus, et al., describes a method for operating a surgical system including a control unit having a vacuum sensor and/or a flow rate sensor, the method including placing a handpiece in an operative relationship with an eye for a surgical procedure and thereafter supplying irrigation fluid to the handpiece while applying a vacuum to the handpiece to aspirate the irrigation fluid from the eye through the handpiece. During fluid aspiration, a vacuum level and/or flow rate is sensed which corresponds to an occlusion of the handpiece and from the sensed vacuum level and/or flow rate, a duration of the occlusion is determined. In response to the determined duration of occlusion, at least one of the handpiece parameters is varied.

U.S. Pat. No. 10,251,983 to Raney, et al., describes methods and apparatuses for automatically switching different aspiration levels to an ocular probe. The probe may be a phacoemulsification probe. A first aspiration level, supplied by a first pump, may be applied to the probe simultaneously with ultrasonic energy. A second aspiration level, supplied by a second pump, may be automatically switched from the first aspiration level. Control feedback of the pumps may be varied according to set thresholds.

U.S. Pat. No. 7,967,777 to Edwards, et al., describes an eye treatment system that is configured for performing an ocular surgical procedure and includes an eye treatment probe, a treatment console including a controller, and an eye treatment cassette for coupling the eye treatment probe with the treatment console. The eye treatment probe is configured to provide at least irrigation fluid to, and aspiration of fluid from, a subject eye. The cassette comprises a cassette body, first and second arcuate ramps, and a holding tank. The cassette has an engagement axis along which elements of the cassette are configured to generally engage with mating elements of the treatment console. The cassette's first arcuate ramp is proximal a first fluidics channel configured to form a first volumetric pump upon engagement with the treatment console. Also, the cassette's second arcuate ramp is proximal a second fluidics channel configured to form a second volumetric pump upon engagement with the treatment console. The cassette also includes a holding tank fluidly that is coupled to the volumetric pumps.

U.S. Pat. No. 9,522,221 to Muri, et al., describes an eye treatment cassette that includes a handpiece, a vacuum source, a holding tank, a collection bag, and a displacement-based pump. The handpiece is configured to aspirate fluids from a patient's eye. The vacuum source communicates with the handpiece. The holding tank is interposed between the handpiece and the vacuum source, and is configured to hold the aspirated fluids. The collection bag is connected to the holding tank for collecting the aspirated fluids. The pump is coupled to the holding tank and is configured to operate while the vacuum source continues to aspirate fluids via the handpiece to drain the aspirated fluids from the holding tank.

U.S. Pat. No. 8,011,909 to Dong describes a vane pump assembly including a cam ring having an elliptical inner bore defining a hydraulic pumping chamber, the pumping chamber having an interior camming surface. The cam ring defines ports for admitting fluid into the pumping chamber. A rotor, within the cam ring, defines a plurality of radial vane slots. A vane assembly is supported in each vane slot to define vane buckets. Each vane assembly has an end dynamic vane seal for reducing leakage between the buckets. Front and rear side plates, separated by an annular spacer, enclose the pumping chamber. The pump assembly may also include floating front and rear rotor seals for reducing radially inward leakage. Each rotor seal is disposed within a groove formed in the rotor, wherein discharge pressure urges the rotor seals axially outward from the pumping chamber to create an effective seal against the respective side plate.

U.S. Pat. No. 4,183,723 to Hansen, et al., describes a vane-type double lobe hydraulic pump having a casing with a rotor having a plurality of slots with each slot mounting a vane for tracking of a surrounding cam ring and porting for pumping from both undervane and intervane pumping chambers. The cam ring has two generally elliptical sections of different contour whereby the volumes of fluid pumped by the vanes in coacting with one of said sections differ from the pumped volumes of the vanes when coacting with the other section. In one embodiment, there are four independent volume outputs while, in other embodiments, valve elements control the output of the pump whereby it may be the total of the pumped fluid or lesser amounts including only the volume pumped by the vanes in coacting with one of said cam ring sections or only part thereof.

SUMMARY

There is provided in accordance with an exemplary embodiment of the present invention, a medical system including a medical instrument including a distal end configured to be inserted into a body part of a living subject, the medical instrument including an irrigation channel and an aspiration channel configured to carry irrigation fluid to the distal end and remove aspirated matter from the distal end, respectively, an irrigation reservoir configured to store the irrigation fluid, a collection receptacle configured to collect the aspirated matter, and a shared vane pump including a pump housing having an inner surface around a pumping chamber, the pump housing including irrigation inlet and outlet ports coupled to the pumping chamber and respectively connected to the irrigation reservoir and the irrigation channel of the medical instrument, and aspiration inlet and outlet ports coupled to the pumping chamber and respectively connected to the aspiration channel and the collection receptacle, and wherein the shared vane pump is configured to simultaneously pump via the pumping chamber, at substantially the same flow rate, the irrigation fluid from the irrigation reservoir to the distal end of the medical instrument through the irrigation channel and the aspirated matter from the distal end of the medical instrument through the aspiration channel to the collection receptacle.

Further in accordance with an exemplary embodiment of the present invention, the shared vane pump includes a rotor disposed in the pumping chamber, the rotor includes an axis about which the rotor is configured to rotate, vane slots disposed radially around the axis, and respective radially movable vanes being disposed in respective ones of the vane slots, and respective pairs of the vanes define respective vane buckets, the rotor is configured to apply a radially outward force to the vanes to maintain contact of the vanes with the inner surface while the rotor is rotated, and the rotor and pump housing are configured to simultaneously pump via the vane buckets a flow of the irrigation fluid from the irrigation inlet port to the irrigation outlet port, and a flow of the aspirated matter from the aspiration inlet port to the aspiration outlet port at substantially the same flow rate.

Still further in accordance with an exemplary embodiment of the present invention, the inner surface has an oval cross-section with two axes of symmetry, the rotor being disposed centrally in the oval cross-section.

Additionally, in accordance with an exemplary embodiment of the present invention, the rotor includes at least one resilient ring member configured to apply the radially outward force to the respective vanes.

Moreover, in accordance with an exemplary embodiment of the present invention, the system includes an auxiliary vane pump including irrigation inlet and outlet ports respectively connected to the irrigation reservoir and the irrigation channel of the medical instrument, and aspiration inlet and outlet ports respectively connected to the aspiration channel and the collection receptacle, and a pump controller configured to control operation of the shared vane pump and the auxiliary vane pump.

Further in accordance with an exemplary embodiment of the present invention, the auxiliary vane pump includes a pump housing having an inner surface around a pumping chamber, the pump housing of the auxiliary vane pump including the irrigation inlet and outlet ports and the aspiration inlet and outlet ports of the auxiliary vane pump coupled to the pumping chamber of the auxiliary vane pump, the auxiliary vane pump being configured to selectively pump via the pumping chamber of the auxiliary vane pump, the irrigation fluid from the irrigation reservoir to the distal end of the medical instrument through the irrigation channel, or the aspirated matter from the distal end of the medical instrument through the aspiration channel to the collection receptacle.

Still further in accordance with an exemplary embodiment of the present invention, the auxiliary vane pump includes a double pump housing including two pumping chambers, the irrigation inlet and outlet ports of the auxiliary vane pump being coupled to a first one of the two pumping chambers and the aspiration inlet and outlet ports being coupled to a second one of the two pumping chambers.

Additionally, in accordance with an exemplary embodiment of the present invention, the pump controller is configured in response to an irrigation flow rate setting of X and an aspiration flow rate setting of Y, X being equal to Y, to operate the shared vane pump to simultaneously pump, at substantially the same flow rate of X, the irrigation fluid from the irrigation reservoir to the distal end of the medical instrument through the irrigation channel and the aspirated matter from the distal end of the medical instrument through the aspiration channel to the collection receptacle, while the auxiliary vane pump is idle, in response to an irrigation flow rate setting of X and an aspiration flow rate setting of Y, X being greater than Y, which is non-zero, to operate the shared vane pump at a flow rate of Y and the auxiliary vane pump to pump the irrigation fluid from the irrigation reservoir to the distal end of the medical instrument through the irrigation channel at a flow rate of X minus Y, in response to an irrigation flow rate setting of X and an aspiration flow rate setting of Y, Y being greater than X, which is non-zero, to operate the shared vane pump at a flow rate of X and the auxiliary vane pump to pump the aspirated matter from the distal end of the medical instrument through the aspiration channel to the collection receptacle at a flow rate of Y minus X, in response to an irrigation flow rate setting of X and an aspiration flow rate setting of zero, to operate the auxiliary vane pump to pump, the irrigation fluid from the irrigation reservoir to the distal end of the medical instrument through the irrigation channel at a flow rate of X, while the shared vane pump is idle, and in response to an irrigation flow rate setting of zero and an aspiration flow rate setting of Y, to operate the auxiliary vane pump to pump, the aspirated matter from the distal end of the medical instrument through the aspiration channel to the collection receptacle at a flow rate of Y, while the shared vane pump is idle.

Moreover, in accordance with an exemplary embodiment of the present invention, the system includes an irrigation line valve disposed in a connection between the irrigation reservoir and the irrigation inlet of the auxiliary vane pump, and an aspiration line valve disposed in a connection between the aspiration channel of the medical instrument and the aspiration inlet of the auxiliary vane pump, and wherein the pump controller is configured to selectively close the irrigation line valve and operate the auxiliary vane pump to pump the aspirated matter from the distal end of the medical instrument through the aspiration channel to the collection receptacle, and close the aspiration line valve and operate the auxiliary vane pump to pump the irrigation fluid from the irrigation reservoir to the distal end of the medical instrument through the irrigation channel.

Further in accordance with an exemplary embodiment of the present invention, the medical instrument includes a phacoemulsification probe.

There is also provided in accordance with another exemplary embodiment of the present invention, a medical method including connecting an irrigation channel and an aspiration channel of a medical instrument, which is configured to be inserted into a body part of a living subject, to an irrigation outlet port and an aspiration inlet port of a shared vane pump, respectively, the irrigation channel and an aspiration channel being configured to carry irrigation fluid to a distal end of the medical instrument and remove aspirated matter from the distal end of the medical instrument, respectively, connecting an irrigation reservoir, which is configured to store the irrigation fluid, to an irrigation inlet port of the shared vane pump, connecting a collection receptacle, which is configured to collect the aspirated matter, to an aspiration outlet port of the shared vane pump, the irrigation inlet and outlet ports and the aspiration inlet and outlet ports being coupled to a pumping chamber of the shared vane pump, and simultaneously pumping via the pumping chamber, at substantially the same flow rate, the irrigation fluid from the irrigation reservoir to the distal end of the medical instrument through the irrigation channel and the aspirated matter from the distal end of the medical instrument through the aspiration channel to the collection receptacle.

Still further in accordance with an exemplary embodiment of the present invention, the method includes connecting the irrigation channel, the aspiration channel, the irrigation reservoir, and the collection receptacle, to an irrigation outlet port, an aspiration inlet port, an irrigation inlet port, and an aspiration outlet port of an auxiliary vane pump, respectively, and controlling operation of the shared vane pump and the auxiliary vane pump.

Additionally, in accordance with an exemplary embodiment of the present invention, the method includes in response to an irrigation flow rate setting of X and an aspiration flow rate setting of Y, X being equal to Y, operating the shared vane pump to simultaneously pump, at substantially the same flow rate of X, the irrigation fluid from the irrigation reservoir to the distal end of the medical instrument through the irrigation channel and the aspirated matter from the distal end of the medical instrument through the aspiration channel to the collection receptacle, while the auxiliary vane pump is idle, in response to an irrigation flow rate setting of X and an aspiration flow rate setting of Y, X being greater than Y, which is non-zero, operating the shared vane pump at a flow rate of Y and the auxiliary vane pump to pump the irrigation fluid from the irrigation reservoir to the distal end of the medical instrument through the irrigation channel at a flow rate of X minus Y, in response to an irrigation flow rate setting of X and an aspiration flow rate setting of Y, Y being greater than X, which is non-zero, operating the shared vane pump at a flow rate of X and the auxiliary vane pump to pump the aspirated matter from the distal end of the medical instrument through the aspiration channel to the collection receptacle at a flow rate of Y minus X, in response to an irrigation flow rate setting of X and an aspiration flow rate setting of zero, operating the auxiliary vane pump to pump, the irrigation fluid from the irrigation reservoir to the distal end of the medical instrument through the irrigation channel at a flow rate of X, while the shared vane pump is idle, and in response to an irrigation flow rate setting of zero and an aspiration flow rate setting of Y, operating the auxiliary vane pump to pump, the aspirated matter from the distal end of the medical instrument through the aspiration channel to the collection receptacle at a flow rate of Y, while the shared vane pump is idle.

Moreover, in accordance with an exemplary embodiment of the present invention, the method includes selectively closing an irrigation line valve disposed in a connection between the irrigation reservoir and the irrigation inlet of the auxiliary vane pump, and operating the auxiliary vane pump to pump the aspirated matter from the distal end of the medical instrument through the aspiration channel to the collection receptacle, and closing an aspiration line valve disposed in a connection between the aspiration channel of the medical instrument and the aspiration inlet of the auxiliary vane pump, and operating the auxiliary vane pump to pump the irrigation fluid from the irrigation reservoir to the distal end of the medical instrument through the irrigation channel.

BRIEF DESCRIPTION OF THE DRAWINGS

The present invention will be understood from the following detailed description, taken in conjunction with the drawings in which.

DETAILED DESCRIPTION OF THE PREFERRED EMBODIMENTS

Overview

When operating on the eye, such as performing cataract surgery, the flows of fluid into and out of the eye are critical. While performing emulsification of the cataract, aspiration is needed to both bring the cataract into contact with the needle of the phacoemulsification probe so that the needle may sculpt and emulsify the cataract and also to remove particles of the cataract from the eye. As fluid and waste matter is removed from the eye an equal amount of fluid needs to be injected into the eye to ensure that adequate fluid is in the eye at all times. Additionally, it is essential that the pressure in the eye does not exceed safe limits.

Therefore, during cataract surgery it is important to control the irrigation and aspiration very carefully to aspirate fluid from the eye as well as irrigate the eye at the same flow rate, which can be set at different values as necessary. Additionally, non-oscillating or minimally oscillating flows are generally needed for the aspiration and irrigation of the eye.

In addition, other flow modes may be needed, such as irrigation without aspiration, aspiration with irrigation, irrigation at a higher flow rate than aspiration and vice-versa.

Peristaltic pumps may be used for different medical applications. However, peristaltic pumps have a relatively long ramp up time until they achieve a steady state making the flow rate difficult to control. Even when the pump achieves steady state, the fluid flow is oscillating. Using two peristaltic pumps, one for irrigation, and one for aspiration, is also problematic as the two pumps may also have different ramp up times as well as other differing characteristics.

In general, when using two separate pumps to provide the same irrigation flow rate and aspiration flow rate, even using a control loop, the irrigation and aspiration flow rates will generally not be the same due to calibration differences between the two pumps. As the volume of the eye is small, even a small difference between the aspiration and irrigation flow rates could cause serious damage.

Exemplary embodiments of the present invention solve the above-described problems by providing a medical system including a medical instrument having a distal end, and an irrigation channel and an aspiration channel to carry irrigation fluid to the distal end and remove aspirated matter from the distal end, respectively. The medical system includes a shared vane pump to pump the irrigation fluid to the distal end via the irrigation channel and pump aspirated matter from the distal end via the aspiration channel. The shared vane pump pumps the irrigation fluid and the aspirated matter at the same time, at substantially the same non-oscillating flow rate, as will be explained in more detail below. The vane pump typically pumps without pulses and fluctuations and reaches a steady state very quickly.

The medical instrument may include a phacoemulsification probe or any other medical instrument, for example, an ENT tool.

The medical system also includes an irrigation reservoir to store the irrigation fluid and a collection receptacle to collect the aspirated matter.

The shared vane pump includes a pump housing having an inner surface around a pumping chamber. The pump housing includes irrigation inlet and outlet ports coupled to the pumping chamber and respectively connected to the irrigation reservoir, and the irrigation channel of the medical instrument. The pump housing also includes aspiration inlet and outlet ports coupled to the pumping chamber and respectively connected to the aspiration channel and the collection receptacle. The shared vane pump simultaneously pumps via the same pumping chamber, at substantially the same flow rate, the irrigation fluid from the irrigation reservoir to the distal end of the medical instrument through the irrigation channel and the aspirated matter from the distal end of the medical instrument through the aspiration channel to the collection receptacle.

The shared vane pump includes a rotor in the pumping chamber. The rotor includes vane slots disposed radially around the axis of the rotor and respective radially movable vanes in respective ones of the vane slots. Respective pairs of the vanes define respective vane buckets in which fluid is pumped around the pumping chamber. The rotor applies a radially outward force to the vanes to maintain contact of the vanes with the inner surface while the rotor is rotated. The outward force may be provided using any suitable element or elements such as resilient ring members.

The inner surface of the pumping chamber is configured so that the buckets provide an expanding volume at the inlet ports and a decreasing volume at the outlet ports so that fluid is drawn into the buckets at the inlet ports and forced out of the buckets at the outlet ports. In some exemplary embodiments the inner surface of the pumping chamber has an oval cross-section with two axes of symmetry, with the rotor being disposed centrally in the oval cross-section.

The inner surface may have any suitable shape as long as the shape causes the size of the vane buckets at each of the inlet ports to be substantially the same size and expand as the rotor is rotated. The term "substantially the same size" is defined so that flow of irrigation fluid and the flow of aspirated matter is pumped at "substantially the same flow rate" as defined below. As the same vane buckets are used by the irrigation fluid and the aspirated matter as the rotor rotates, the size and configuration of the vane buckets does not contribute to calibration errors between the irrigation and aspiration flow rates. Calibration errors between the irrigation and aspiration flow rates may result from the shape of the pumping chamber and the position of the axis of the rotor with respect to the pumping chamber.

The inlet ports and the outlets ports are arranged around the pumping chamber so that irrigation fluid may enter the irrigation inlet port and exit the irrigation outlet port, while the aspirated matter may enter the aspiration inlet port and exit the aspiration outlet port, and while the irrigation and aspiration flows are in different sections of the pumping chamber. For example, irrigation fluid may be pumped in the upper section of the pumping chamber while the aspirated matter is pumped in the lower section of the pumping chamber.

Therefore, the rotor and pump housing are designed to simultaneously pump via the vane buckets a flow of the irrigation fluid from the irrigation inlet port to the irrigation outlet port, and a flow of the aspirated matter from the aspiration inlet port to the aspiration outlet port at substantially the same flow rate. The term "substantially the same flow rate" as used in the specification and claims, is defined as the flow rate of the irrigation fluid being within 1 percent of the flow rate of the aspirated matter.

Some exemplary embodiments also include an auxiliary vane pump, which may include irrigation inlet and outlet ports respectively connected to the irrigation reservoir and the irrigation channel of the medical instrument, and aspiration inlet and outlet ports respectively connected to the aspiration channel and the collection receptacle. The auxiliary vane pump may selectively pump the irrigation fluid or the aspirated matter under the control of a pump controller.

In some exemplary embodiments, the auxiliary vane pump may be a dual inlet and outlet pump to pump both the irrigation fluid and the aspirated matter via the same pumping chamber (but not at the same time). In these exemplary embodiments, the auxiliary vane pump includes a pump housing having an inner surface around a pumping chamber. The pump housing of the auxiliary vane pump includes irrigation inlet and outlet ports and aspiration inlet and outlet ports coupled to the pumping chamber of the auxiliary vane pump.

An irrigation line valve may be placed in a connection between the irrigation reservoir and the irrigation inlet of the auxiliary vane pump. An aspiration line valve may be placed in a connection between the aspiration channel of the medical instrument and the aspiration inlet of the auxiliary vane pump. The pump controller may selectively open and close of the valves to control which flow (irrigation fluid or aspirated matter) is pumped via the auxiliary vane pump.

In some exemplary embodiments, the auxiliary vane pump may include a double pump housing including two pumping chambers with irrigation inlet and outlet ports being coupled to a first one of the pumping chambers and aspiration inlet and outlet ports being coupled to a second one of the pumping chambers.

In some exemplary embodiments, the auxiliary pump may comprise two single vane pumps to separately pump the irrigation fluid and the aspirated matter.

The pump controller controls operation of the shared vane pump and the auxiliary vane pump. The pump controller may operate the shared vane pump to pump the irrigation fluid and the aspirated matter at the same flow rate, while the auxiliary pump is idle. Alternatively, the pump controller may operate the auxiliary pump to pump either the irrigation fluid or the aspirated matter while the shared vane pump is idle. Alternatively, the pump controller may operate the auxiliary pump to pump either the irrigation fluid or the aspirated matter while the shared vane pump is pumping both the irrigation fluid and the aspirated matter.

The different modes of operation of the shared vane pump and the auxiliary vane pump are now described in more detail. The irrigation flow rate and the aspiration flow rate may be set via a suitable user interface. For example, the irrigation flow rate may be set to X and the aspiration flow rate may be set to Y.

If X is equal to Y, the pump controller may operate the shared vane pump to simultaneously pump, at substantially the same flow rate of X (or Y), the irrigation fluid from the irrigation reservoir to the distal end of the medical instrument through the irrigation channel and the aspirated matter from the distal end of the medical instrument through the aspiration channel to the collection receptacle, while the auxiliary vane pump is idle.

If X is greater than Y, which is non-zero, the pump controller may operate the shared vane pump at a flow rate of Y and the auxiliary vane pump to pump the irrigation fluid from the irrigation reservoir to the distal end of the medical instrument through the irrigation channel at a flow rate of X minus Y, while the aspiration line valve is closed. For example, if X, the irrigation flow rate setting is 15 ml (milliliters) per minute and Y, the aspiration flow rate setting is 10 ml per minute, the shared vane pump operates at a flow rate of 10 ml per minute to pump both irrigation fluid and the aspirated matter, while the auxiliary vane pump pumps irrigation fluid at 5 ml per minute.

If Y is greater than X, which is non-zero, the pump controller may operate the shared vane pump at a flow rate of X and the auxiliary vane pump to pump the aspirated matter from the distal end of the medical instrument through the aspiration channel to the collection receptacle at a flow rate of Y minus X, while the irrigation line valve is closed.

If X is non-zero and Y is zero, the pump controller may operate the auxiliary vane pump to pump the irrigation fluid from the irrigation reservoir to the distal end of the medical instrument through the irrigation channel at a flow rate of X, while the aspiration line valve is closed, and while the shared vane pump is idle.

If X is zero, and Y is non-zero, the pump controller may operate the auxiliary vane pump to pump the aspirated matter from the distal end of the medical instrument through the aspiration channel to the collection receptacle at a flow rate of Y, while the irrigation line valve is closed, and while the shared vane pump is idle.

System Description

Figure 1A:
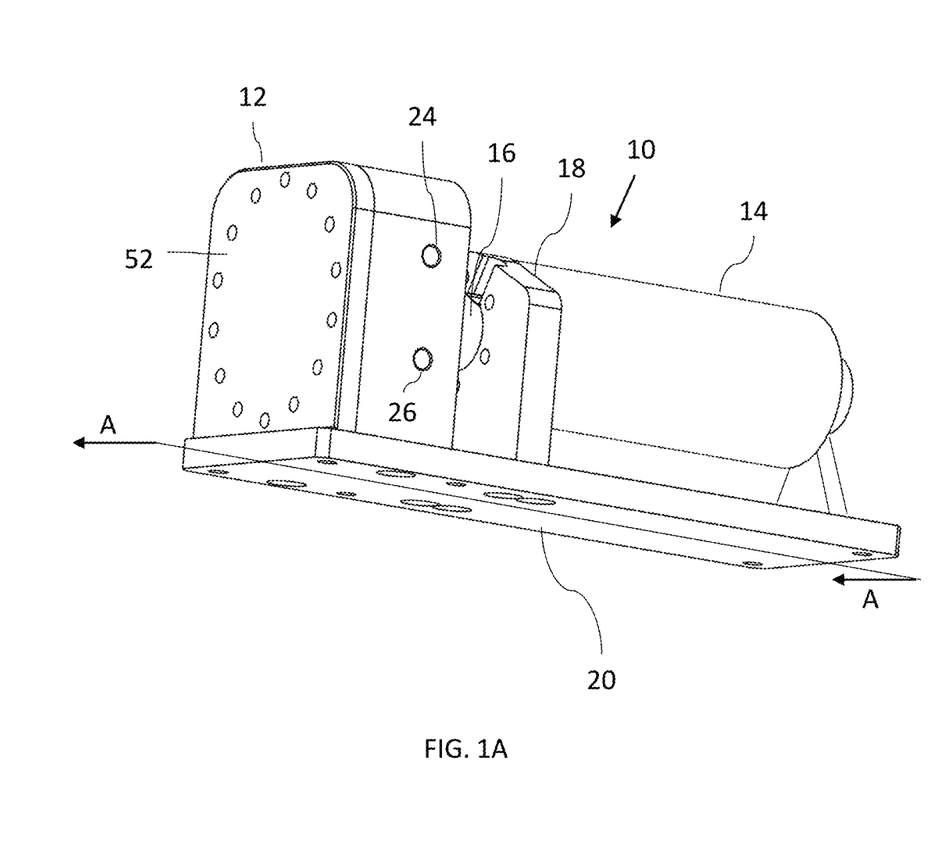
FIGS. 1A and 1B are schematic views of a vane pump constructed and operative in accordance with an embodiment of the present invention.
Figure 1B:
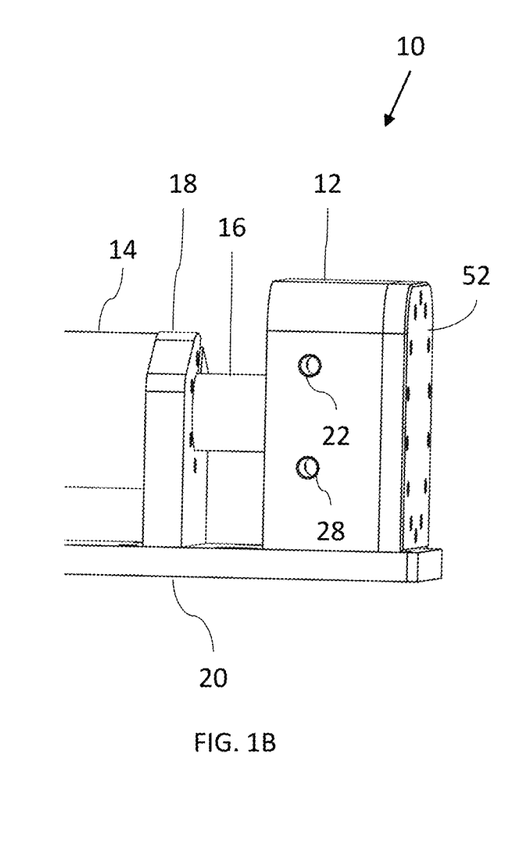

Reference is now made to FIGS. 1A and 1B, which are schematic views of a vane pump 10 constructed and operative in accordance with an embodiment of the present invention. The vane pump 10 includes a pump housing 12, a motor 14, a drive shaft 16, a drive shaft support 18, and a base 20. The pump housing 12, the drive shaft support 18, and the motor 14 are secured to the base 20. The motor 14 drives the drive shaft 16 which turns a rotor in the pump housing 12 described in more detail with reference to FIG. 2. The pump housing 12 includes an irrigation inlet port 22 (FIG. 1B), an irrigation outlet port 24 (FIG. 1A), an aspiration inlet port 26 (FIG. 1A) and an aspiration outlet port 28 (FIG. 1B).

Figure 2:
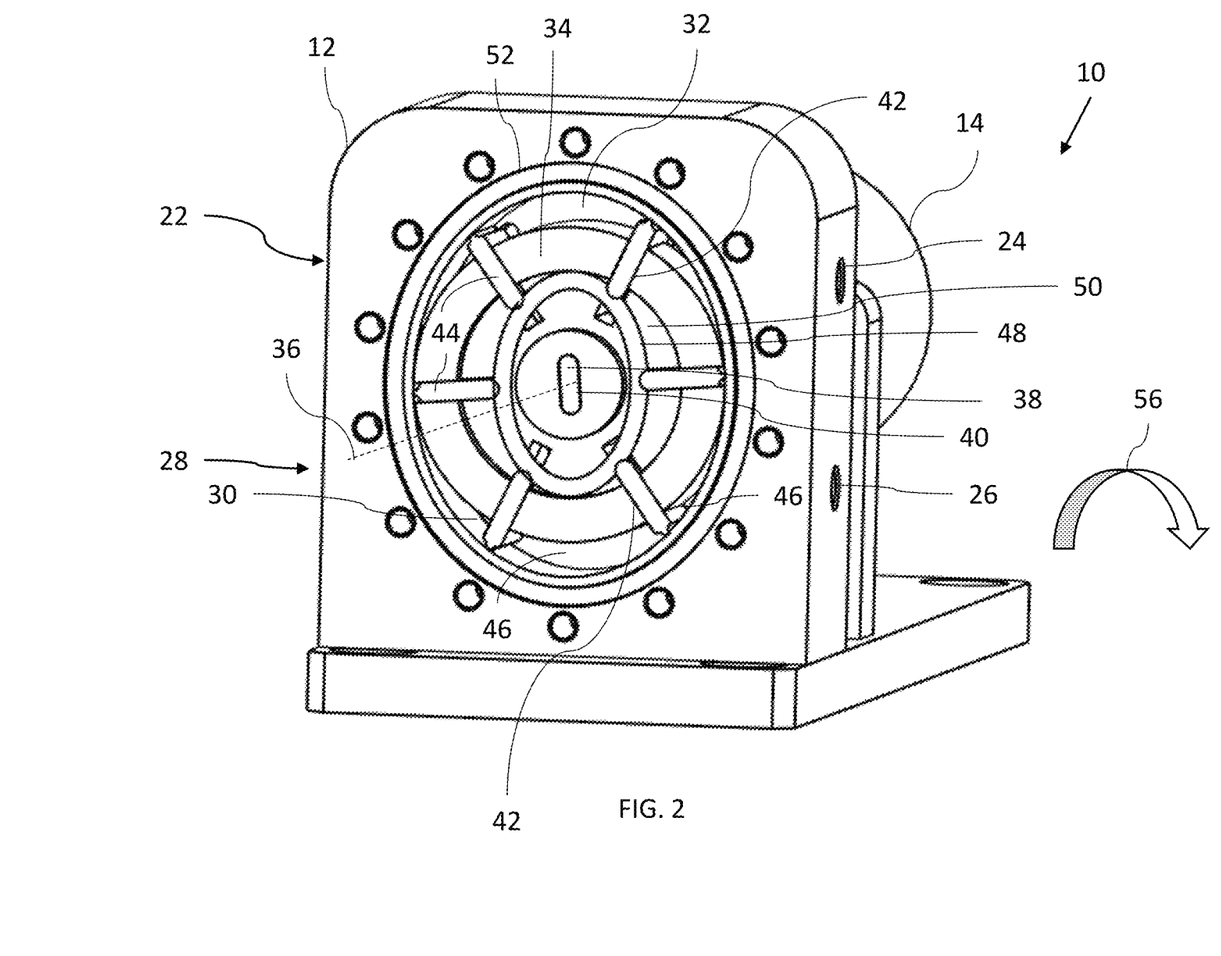
FIG. 2 is a cut-away view of the vane pump of FIGS. 1A and 1B.
Figure 6:
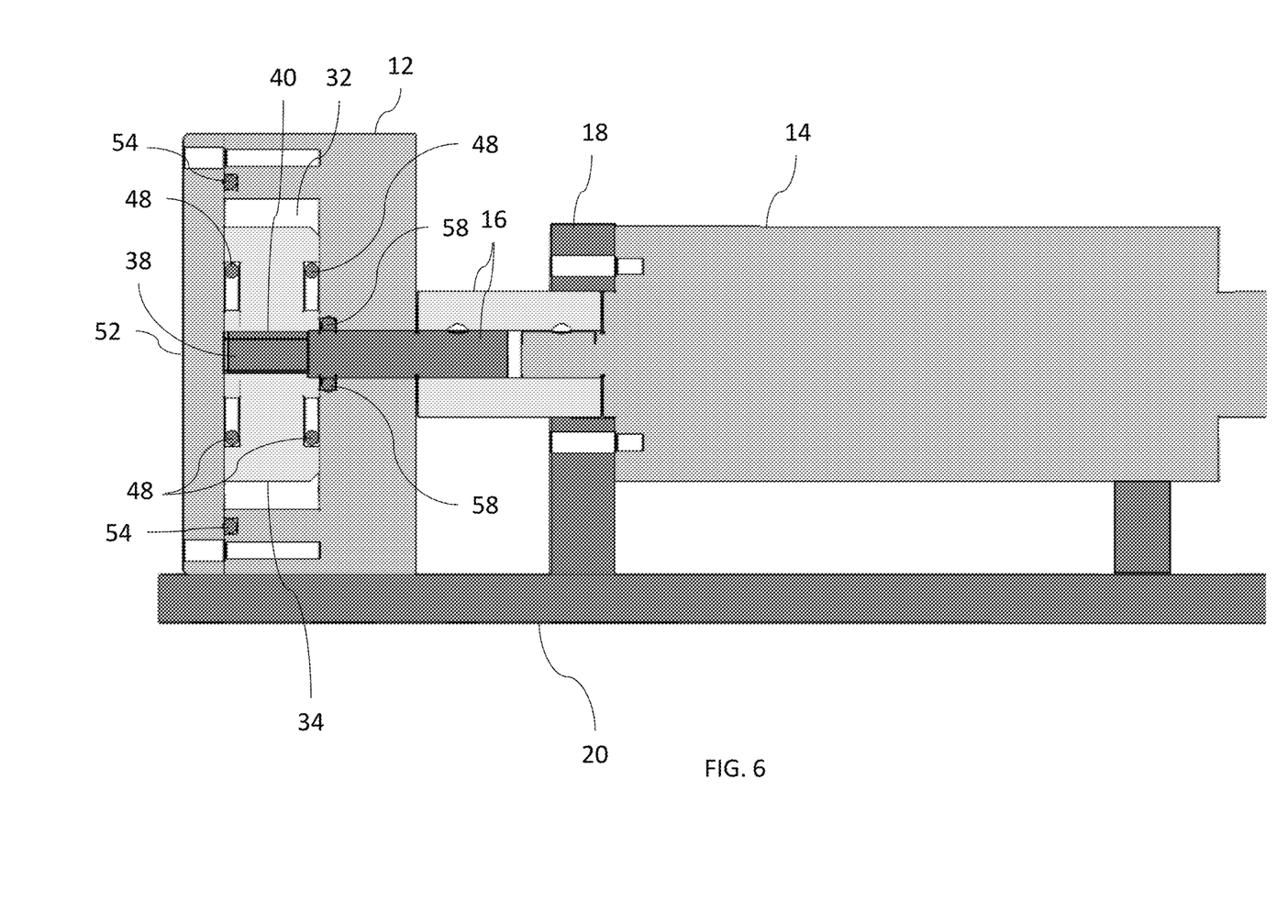
FIG. 6 is a cross-section along line A-A of FIG. 1A.

Reference is now made to FIG. 2, which is a cut-away view of the vane pump 10 of FIGS. 1A and 1B. The pump housing 12 has an inner surface 30 around a pumping chamber 32. The pumping chamber 32 is shown more clearly in FIGS. 3A and 3B. The irrigation inlet port 22 and the irrigation outlet port 24 are coupled to the pumping chamber 32. The aspiration inlet port 26 and the aspiration outlet port 28 are coupled to the pumping chamber 32. The vane pump 10 includes a rotor 34 disposed in the pumping chamber 32. The rotor 34 has an axis of rotation 36 about which the rotor 34 is configured to rotate. The drive shaft 16 (FIGS. 1A and B) includes an element 38 disposed in a slot 40 at the center of the rotor 34 to support the rotor 34 on the axis 36 in the pumping chamber 32 and rotate the rotor 34 when the motor 14 is actuated. The rotor 34 includes vane slots 42 (only some labeled for the sake of simplicity) disposed radially around the axis 36. The rotor 34 includes respective radially movable vanes 44 (only some labeled for the sake of simplicity) being disposed in respective ones of the vane slots 42. Respective pairs of the vanes 44 define respective vane buckets 46 (only some labeled for the sake of simplicity) in which fluid is pumped around the pumping chamber 32. The rotor 34 is configured to apply a radially outward force to the vanes 44 to maintain contact of the vanes 44 with the inner surface 30 while the rotor 34 is rotated. In some exemplary embodiments, the rotor 34 includes at least one resilient ring member 48 configured to apply the radially outward force to the respective vanes 44. The rotor 34 includes one resilient ring member 48 on one side of the rotor 34 as shown in FIG. 2, and another resilient ring member 48 on the other side of the rotor 34 as shown in FIG. 6. The resilient ring members 48 rest in respective inset sections 50 of the rotor 34 and apply an outward force on the vanes 44.

The elements of the vane pump 10 may be formed from any suitable material, for example, metal and/or plastic. The surfaces which come into contact with the fluids are generally formed from a biocompatible metal or plastic, for example, but not limited to, stainless steel, titanium, polypropylene, and/or polytetrafluoroethylene (PTFE).

The inner surface 30 of the pumping chamber 32 is configured so that the buckets 46 provide an expanding volume at the inlet ports 22, 26 and a decreasing volume at the outlet ports 24, 28 so that fluid is drawn into the buckets 46 at the inlet ports 22, 26 and forced out of the buckets 46 at the outlet ports 24, 28, respectively. In some exemplary embodiments the inner surface 30 of the pumping chamber 32 has an oval cross-section with two axes of symmetry, with the rotor 34 being disposed centrally in the oval cross-section. The inner surface 30 may have any suitable shape as long as the shape causes the size of the vane buckets 46 at each of the inlet ports 22, 26 to be substantially the same size, and expand as the rotor 34 is rotated. As the same vane buckets 46 are used by the irrigation fluid and the aspirated matter as the rotor 34 rotates, the size and configuration of the vane buckets 46 does not contribute to calibration errors between the irrigation and aspiration flow rates. Calibration errors between the irrigation and aspiration flow rates may result from the shape of the pumping chamber 32 and the position of the axis 36 with respect to the pumping chamber 32.

The dimensions of the various elements in the vane pump 10 may be any suitable dimensions depending on the pumping requirements of the medical application. For example in some medical applications, the depth of the pumping chamber 32 may be in the range of 1 to 15 cm, the outer diameter of the rotor 34 may be in the range of 3 to 20 cm, and the maximum gap between the rotor 34 and the inner surface 30 of the pumping chamber 32 may be in the range of 0.25 to 15 cm. In other medical applications, other values may be used.

The inlet ports 22, 26 and the outlets ports 24, 28 are arranged around the pumping chamber 32 so that irrigation fluid may enter the irrigation inlet port 22 and exit the irrigation outlet port 24, while aspirated matter may enter the aspiration inlet port 26 and exit the aspiration outlet port 28, while the irrigation and aspiration flows are in different sections of the pumping chamber 32. For example, irrigation fluid may be pumped in the upper section of the pumping chamber 32 while the aspirated matter is pumped in the lower section of the pumping chamber 32, according to the example of FIG. 2. In some exemplary embodiments, the irrigation inlet port 22 and the irrigation outlet port 24 may be disposed on the same side of the pumping chamber 32 while the aspiration inlet port 26 and the aspiration outlet port 28 are disposed on the other side of the pumping chamber 32.

Therefore, the rotor 34 and pump housing 12 are configured to simultaneously pump via the vane buckets 46, a flow of the irrigation fluid from the irrigation inlet port 22 to the irrigation outlet port 24, and a flow of the aspirated matter from the aspiration inlet port 26 to the aspiration outlet port 28 at substantially the same flow rate.

The flow rate of simultaneous pumping may be changed by changing the speed of the motor 14. In the example given in FIG. 2, the rotor 34 is rotated in a clock-wise direction as shown by arrow 56. In other exemplary embodiments the direction of rotation may be reversed. The rotation speed of the rotor 34 may be set to any suitable value subject to a minimum speed to draw fluid into the vane buckets 46, and a maximum speed up to which the motor 14 and the mechanical parts of the vane pump 10 may operate.

The pump housing 12 includes a vane seal 54 to seal prevent fluid leakage between the pumping chamber 32 and a cover 52 (FIGS. 1A, 1B, 6) of the pump housing 12. The vane seal 54 may include any suitable biocompatible sealant material such as PTFE or silicone.

Figure 3A:
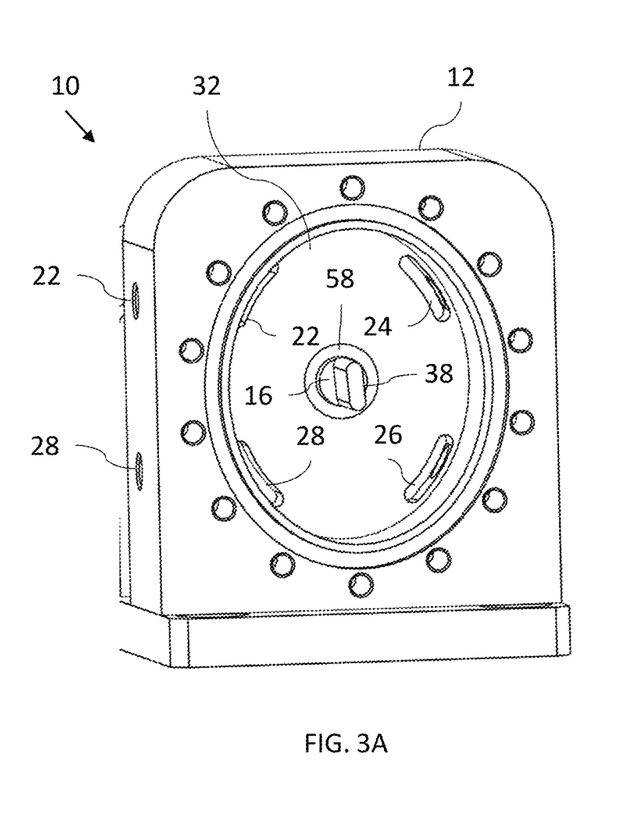
FIGS. 3A and 3B are schematic views of a pumping chamber of the vane pump of FIGS. 1A and 1B.
Figure 3B:
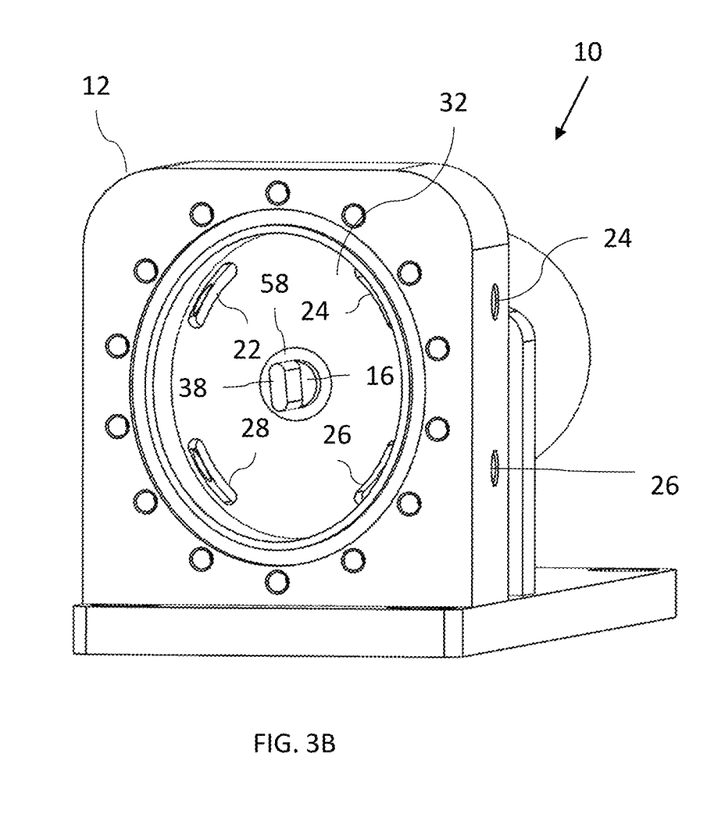

Reference is now made to FIGS. 3A and 3B, which are schematic views of the pumping chamber 32 of the vane pump 10 of FIGS. 1A and 1B. FIGS. 3A and 3B show the pumping chamber 32 emptied of the rotor 34 (FIG. 2). FIG. 3A shows the irrigation inlet port 22 and the aspiration outlet port 28 on the outside of the pump housing 12 as well as the internal portions of the irrigation inlet port 22, the irrigation outlet port 24, the aspiration inlet port 26, and the aspiration outlet port 28 inside the pumping chamber 32. FIG. 3B shows the irrigation outlet port 24 and the aspiration inlet port 26 on the outside of the pump housing 12 as well as the internal portions of the irrigation inlet port 22, irrigation outlet port 24, aspiration inlet port 26, and aspiration outlet port 28 inside the pumping chamber 32. FIGS. 3A and 3B also show the element 38 of the drive shaft 16 centrally disposed at the back of the pumping chamber 32 with a drive shaft seal 58 to prevent fluid leakage between the rotor 34 (FIG. 2) and the drive shaft 16. The positioning of the drive shaft seal 58 is shown more clearly in FIG. 6. The drive shaft seal 58 may include any suitable biocompatible sealant material such as PTFE or silicone.

Figure 4:
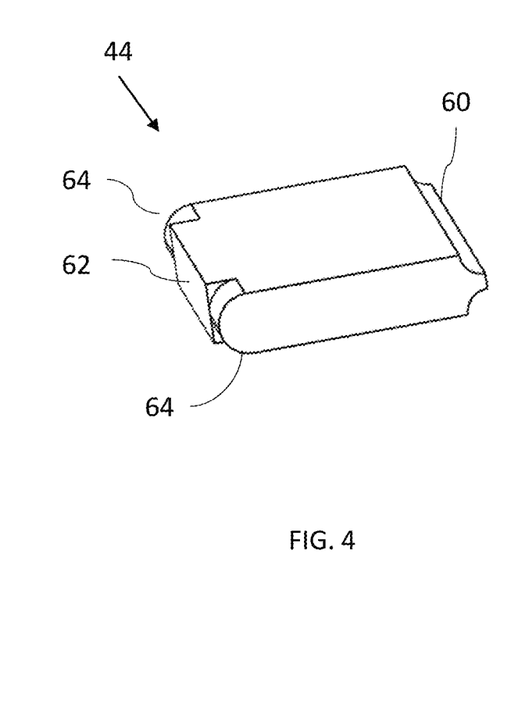
FIG. 4 is a schematic view of a vane for use in the vane pump of FIGS. 1A and 1B.

Reference is now made to FIG. 4, which is a schematic view of one of the vanes 44 for use in the vane pump 10 of FIGS. 1A and 1B. The vane 44 includes a tapered end 60 which comes into contact with the inner surface 30 (FIG. 2) of the pumping chamber 32 (FIG. 2). The tapered end 60 is typically formed from a material which provides a fluid seal between adjacent vane buckets 46 (FIG. 2) as well as having low friction so that the tapered end 60 slides easily around the inner surface 30 as the rotor 34 (FIG. 2) is rotated. The tapered end 60 may be formed from any suitable material for example, but not limited to, polypropylene, and/or PTFE. The vane 44 has an end 62 disposed closest to the axis of rotation 36 of the rotor 34 and includes rounded edges 64 which are configured to abut the resilient ring members 48 (FIGS. 2 and 6). The remainder of the vane 44 may be formed from any suitable material, for example, metal and/or plastic. The surfaces which come into contact with the fluids are generally formed from a biocompatible metal or plastic, for example, but not limited to, stainless steel, titanium, polypropylene, and/or polytetrafluoroethylene (PTFE).

Figure 5:
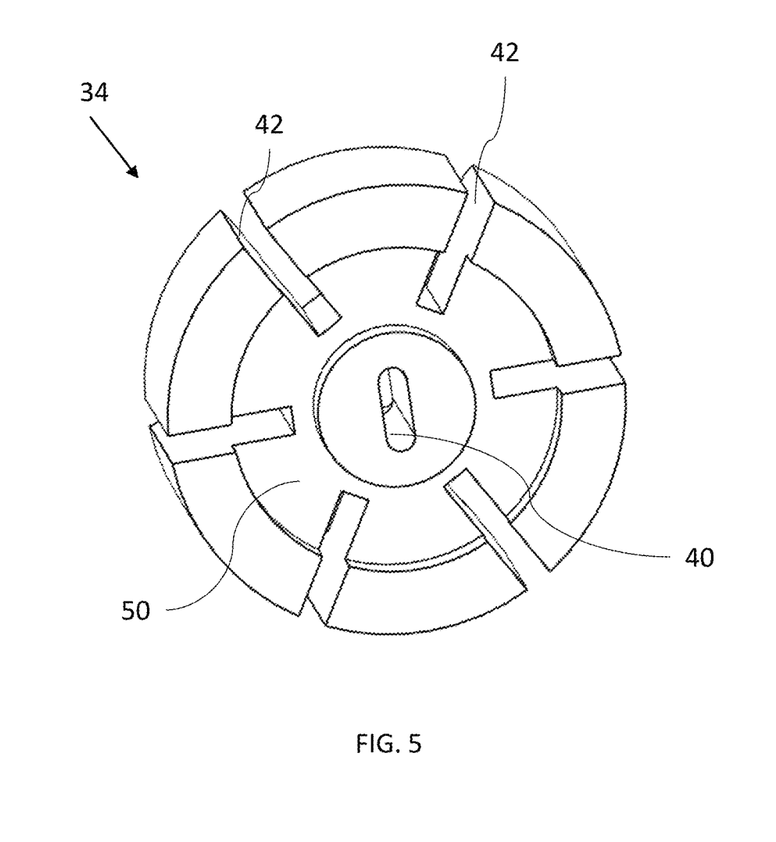
FIG. 5 is a schematic view of a rotor for use in the vane pump of FIGS. 1A and 1B.

Reference is now made to FIG. 5, which is a schematic view of the rotor 34 for use in the vane pump 10 of FIGS. 1A and 1B. FIG. 5 shows the vane slots 42 (only some labeled for the sake of simplicity), the slot 40 located at the center of the rotor 34 and extends from one side of the rotor 34 to the other, and one of the inset sections 50. The other inset section 50 is on the reverse side of the rotor 34 and is not visible in FIG. 5. The depth of each inset section 50 is deep enough to accept one of the resilient ring members 48 (FIG. 2) therein.

Reference is now made to FIG. 6, which is a cross-section along line A-A of FIG. 1A. FIG. 6 shows the motor 14 (connected to the drive shaft 16), the drive shaft support 18, and the pump housing 12 mounted on the base 20. The element 38 is shown at the end of the drive shaft 16 and is inserted into the slot 40 of the rotor 34. The rotor 34 is shown disposed in the pump housing 12 with the resilient ring member 48 disposed either side of the rotor 34. The vane seal 54 provides a seal between the cover 52 of the pump housing 12 and the pumping chamber 32. The drive shaft seal 58 provides a seal between the rear of the rotor 34 and the drive shaft 16.

Figure 7:
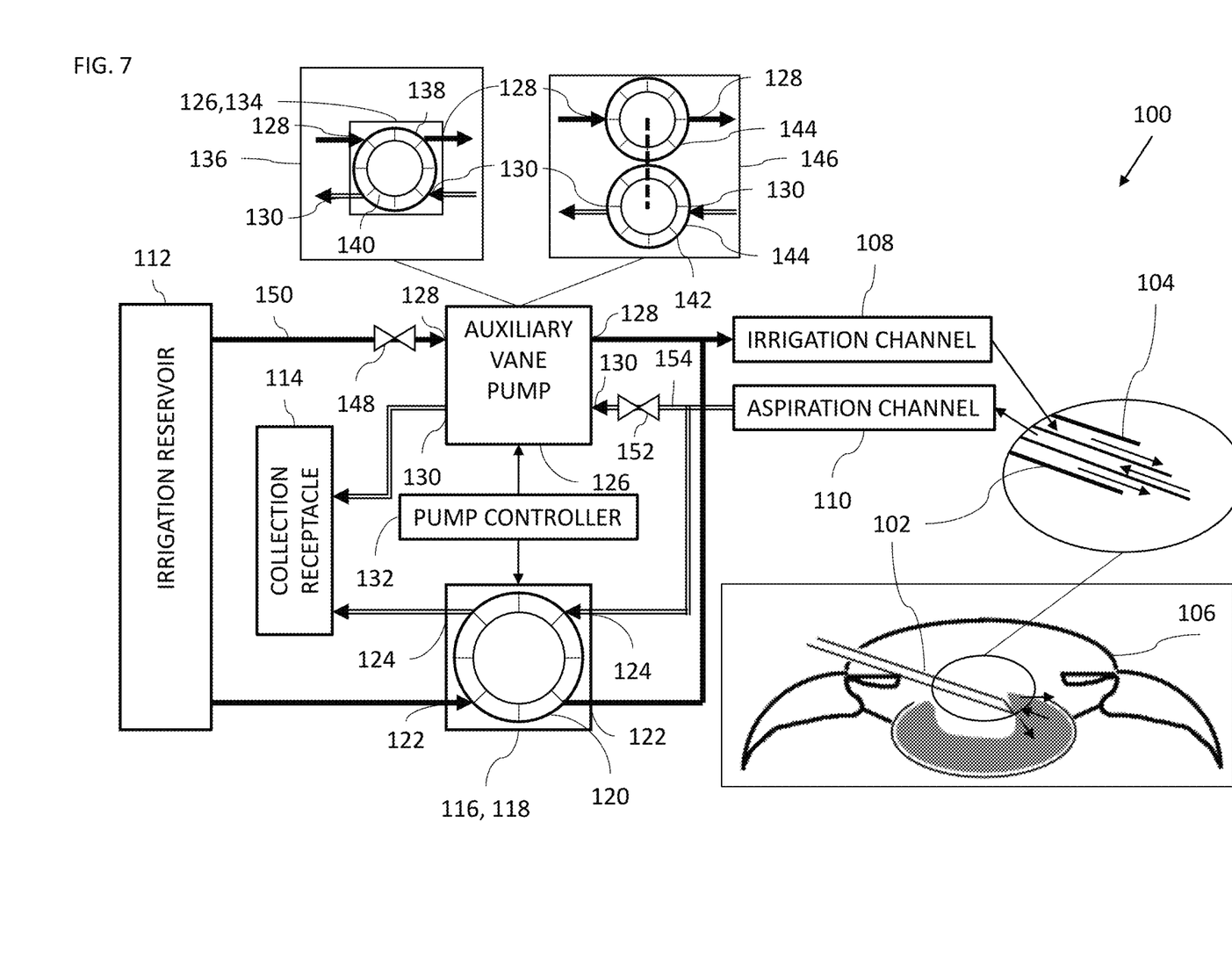
FIG. 7 is a medical irrigation and aspiration system constructed and operative in accordance with an embodiment of the present invention.

Reference is now made to FIG. 7, which is a medical irrigation and aspiration system 100 constructed and operative in accordance with an exemplary embodiment of the present invention. The system 100 includes a medical instrument 102 including a distal end 104 configured to be inserted into a body part 106 (e.g., an eye) of a living subject. The medical instrument 102 includes an irrigation channel 108 and an aspiration channel 110 configured to carry irrigation fluid to the distal end 104 and remove aspirated matter from the distal end 104, respectively. In some exemplary embodiments, the medical instrument 102 includes a phacoemulsification probe. The system 100 includes an irrigation reservoir 112 configured to store the irrigation fluid, and a collection receptacle 114 configured to collect the aspirated matter.

The system 100 includes a shared vane pump 116 including a pump housing 118 having a pumping chamber 120. The shared vane pump 116 may be implemented according to the description of the vane pump 10 of FIGS. 1-6. The pump housing 118 includes irrigation inlet and outlet ports 122 respectively connected to the irrigation reservoir 112 and the irrigation channel 108 of the medical instrument 104. The pump housing 118 includes aspiration inlet and outlet ports 124 respectively connected to the aspiration channel 110 and the collection receptacle 114. The shared vane pump 116 is configured to simultaneously pump via the pumping chamber 120, at substantially the same flow rate (e.g., a volume per unit time), the irrigation fluid from the irrigation reservoir 112 to the distal end 104 of the medical instrument 102 through the irrigation channel 108 and the aspirated matter from the distal end 104 of the medical instrument 102 through the aspiration channel 110 to the collection receptacle 114.

The system 100 also includes an auxiliary vane pump 126. The auxiliary vane pump 126 includes irrigation inlet and outlet ports 128 respectively connected to the irrigation reservoir 112 and the irrigation channel 108 of the medical instrument 102. The auxiliary vane pump 126 also includes aspiration inlet and outlet ports 130 respectively connected to the aspiration channel 110 and the collection receptacle 114.

The system 100 includes a pump controller 132 configured to control operation of the shared vane pump 116 and the auxiliary vane pump 126. The functionality of the pump controller 132 is described in more detail below and with reference to FIG. 8. In practice, some or all of the functions of the pump controller 132 may be combined in a single physical component or, alternatively, implemented using multiple physical components. These physical components may comprise hard-wired or programmable devices, or a combination of the two. In some exemplary embodiments, at least some of the functions of the pump controller 132 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

In some exemplary embodiments, the auxiliary vane pump 126 as shown in inset 136 comprises a pump housing 134 having an inner surface 138 around a pumping chamber 140 and may be implemented according to the description of the vane pump 10 of FIGS. 1-6. The pump housing 134 of the auxiliary vane pump 126 includes the irrigation inlet and outlet ports 128 and the aspiration inlet and outlet ports 130 coupled to the pumping chamber 140. The auxiliary vane pump 126 is configured to selectively pump via the pumping chamber 140, the irrigation fluid from the irrigation reservoir 112 to the distal end 104 of the medical instrument 102 through the irrigation channel 108, or the aspirated matter from the distal end 104 of the medical instrument 102 through the aspiration channel 110 to the collection receptacle 114.

In some exemplary embodiments, the auxiliary vane pump 126 auxiliary vane pump comprises a double pump housing 142 including two pumping chambers 144 as shown in inset 146. The irrigation inlet and outlet ports 128 are coupled to a first one of the pumping chambers 144 and the aspiration inlet and outlet ports 130 are coupled to a second one of the pumping chambers 144. The rotor in each pumping chamber may be driven by a common motor and common drive shaft.

The system 100 includes an irrigation line valve 148 disposed in a connection 150 between the irrigation reservoir 112 and the irrigation inlet 128 of the auxiliary vane pump 126. The system 100 also includes an aspiration line valve 152 disposed in a connection 154 between the aspiration channel 110 of the medical instrument 102 and the aspiration inlet 130 of the auxiliary vane pump 126.

The pump controller 132 is configured to selectively perform the following, but generally at different times: (a) close the irrigation line valve 128 and operate the auxiliary vane pump 126 to pump the aspirated matter from the distal end 104 of the medical instrument 102 through the aspiration channel 110 to the collection receptacle 114; and (b) close the aspiration line valve 152 and operate the auxiliary vane pump 126 to pump the irrigation fluid from the irrigation reservoir 112 to the distal end 104 of the medical instrument 102 through the irrigation channel 108.

Figure 8:
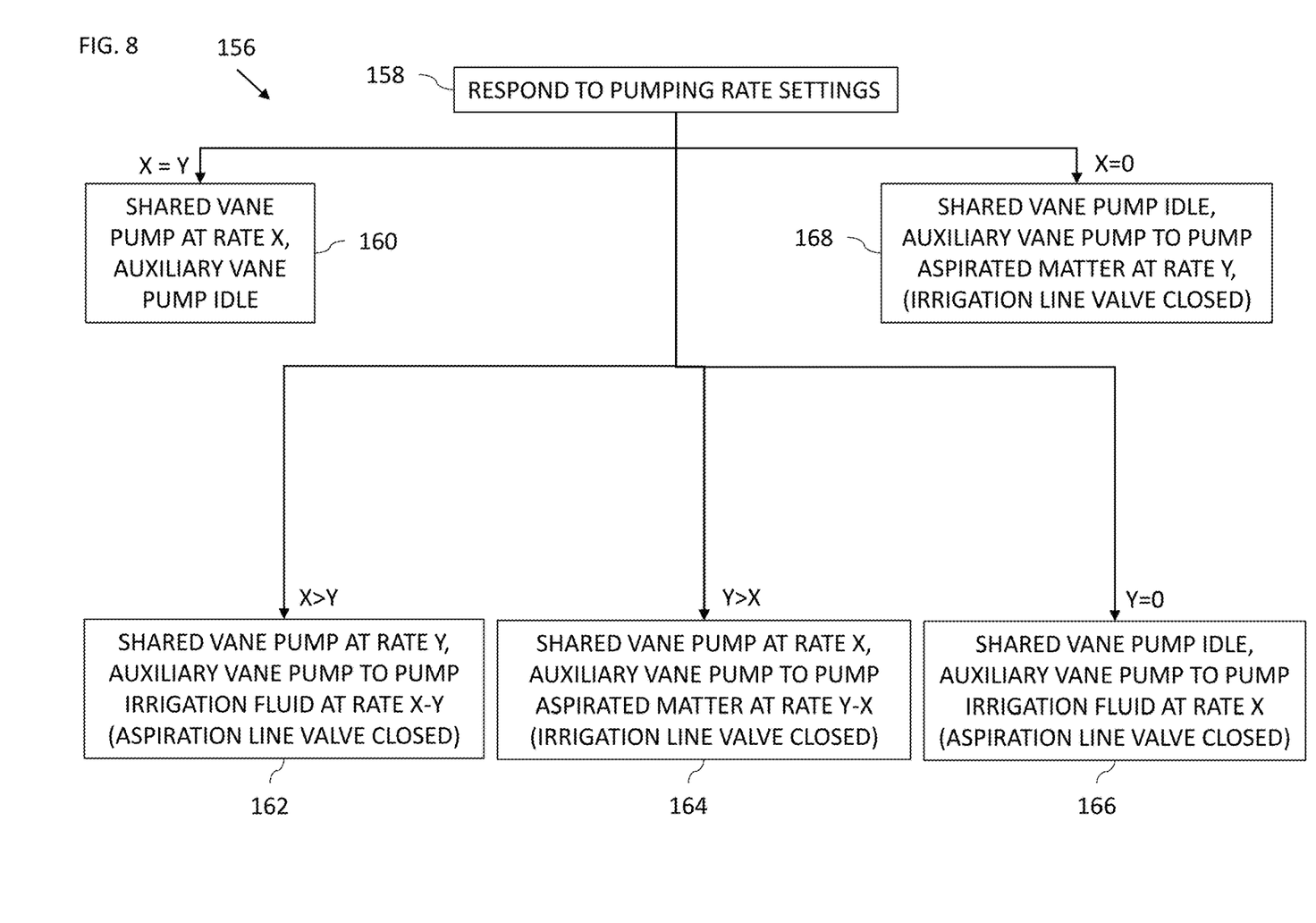
FIG. 8 is a flowchart including steps in a method of operation of the system of FIG. 7.

Reference is now made to FIG. 8, which is a flowchart 156 including steps in a method of operation of the system 100 of FIG. 7. Reference is also made to FIG. 7. The irrigation flow rate and the aspiration flow rate may be set via a suitable user interface (e.g., using dials, a computer user interface, and/or an LED display with setting buttons). For example, the irrigation flow rate may be set to X and the aspiration flow rate may be set to Y. The pump controller 132 is configured to respond (block 158) to the pumping flow rate settings of X and Y as follows.

The pump controller 132 is configured, in response to X being equal to Y, to operate (block 160) the shared vane pump 116 to simultaneously pump, at substantially the same flow rate of X, the irrigation fluid from the irrigation reservoir 112 to the distal end 104 of the medical instrument 102 through the irrigation channel 108 and the aspirated matter from the distal end 104 of the medical instrument 102 through the aspiration channel 110 to the collection receptacle 114, while the auxiliary vane pump 126 is idle.

The pump controller 132 is configured, in response to X being greater than Y, which is non-zero, to operate (block 162) the shared vane pump 116 at a flow rate of Y and the auxiliary vane pump 126 to pump the irrigation fluid from the irrigation reservoir 112 to the distal end 104 of the medical instrument 102 through the irrigation channel 108 at a flow rate of X minus Y, while the aspiration line valve 152 is closed.

The pump controller 132 is configured, in response to Y being greater than X, which is non-zero, to operate (block 164) the shared vane pump 116 at a flow rate of X and the auxiliary vane pump 126 to pump the aspirated matter from the distal end 104 of the medical instrument 102 through the aspiration channel 110 to the collection receptacle 114 at a flow rate of Y minus X, while the irrigation line valve 148 is closed.

The pump controller 132 is configured, in response Y being zero, and X being non-zero, to operate (block 166) the auxiliary vane pump 126 to pump the irrigation fluid from the irrigation reservoir 112 to the distal end 104 of the medical instrument 102 through the irrigation channel 108 at a flow rate of X, while the shared vane pump 116 is idle, and while the aspiration line valve 152 is closed.

The pump controller 132 is configured, in response to X being zero, and Y being non-zero, to operate (block 168) the auxiliary vane pump 126 to pump, the aspirated matter from the distal end 104 of the medical instrument 102 through the aspiration channel 110 to the collection receptacle 114 at a flow rate of Y, while the shared vane pump 116 is idle, and while the irrigation line valve 148 is closed.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values +/−20 percent of the recited value, e.g. "about 90 percent" may refer to the range of values from 71 percent to 99 percent.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system comprising:
   a medical instrument including a distal end configured to be inserted into a body part of a living subject, the medical instrument including an irrigation channel and an aspiration channel configured to carry irrigation fluid to the distal end and remove aspirated matter from the distal end, respectively;
   an irrigation reservoir configured to store the irrigation fluid;
   a collection receptacle configured to collect the aspirated matter;
   a shared vane pump comprising a pump housing having an inner surface around a pumping chamber, the pump housing including:
      an irrigation inlet port coupled with the pumping chamber of the shared vane pump and coupled with the irrigation reservoir via a first irrigation line;
      an irrigation outlet port coupled with the pumping chamber of the shared vane pump and coupled with the irrigation channel of the medical instrument;
      an aspiration inlet port coupled with the pumping chamber of the shared vane pump and coupled with the aspiration channel; and
      an aspiration outlet port coupled with the pumping chamber of the shared vane pump and coupled with the collection receptacle via a first aspiration line, and wherein
   the shared vane pump is configured to simultaneously pump via the pumping chamber, at substantially the same flow rate, the irrigation fluid from the irrigation reservoir to the distal end of the medical instrument through the first irrigation line and the irrigation channel and the aspirated matter from the distal end of the medical instrument through the aspiration channel and the first aspiration line to the collection receptacle;
   an auxiliary vane pump comprising:
      at least one pumping chamber;
      an irrigation inlet port coupled with the at least one pumping chamber of the auxiliary vane pump and coupled with the irrigation reservoir via a second irrigation line;
      an irrigation outlet port coupled with the at least one pumping chamber of the auxiliary vane pump and coupled with the irrigation channel of the medical instrument;
      an aspiration inlet port coupled with the at least one pumping chamber of the auxiliary vane pump and coupled with the aspiration channel; and
      an aspiration outlet port coupled with the at least one pumping chamber of the auxiliary vane pump and coupled with the collection receptacle via a second aspiration line,
   the auxiliary vane pump configured to selectively pump the irrigation fluid from the irrigation reservoir to the distal end of the medical instrument through the second irrigation line and the irrigation channel, or the aspirated matter from the distal end of the medical instrument through the aspiration channel and the second aspiration line to the collection receptacle; and
   a pump controller configured to control operation of the shared vane pump and the auxiliary vane pump.

2. The system according to claim 1, wherein:
   the shared vane pump comprises a rotor disposed in the pumping chamber;
   the rotor includes:
      an axis about which the rotor is configured to rotate;
      vane slots disposed radially around the axis; and
      respective radially movable vanes being disposed in respective ones of the vane slots; and
   respective pairs of the vanes define respective vane buckets;
   the rotor is configured to apply a radially outward force to the vanes to maintain contact of the vanes with the inner surface while the rotor is rotated; and
   the rotor and pump housing are configured to simultaneously pump via the vane buckets a flow of the irrigation fluid from the irrigation inlet port to the irrigation outlet port; and a flow of the aspirated matter from the aspiration inlet port to the aspiration outlet port at substantially the same flow rate.

3. The system according to claim 2, wherein the inner surface has an oval cross-section with two axes of symmetry, the rotor being disposed centrally in the oval cross-section.

4. The system according to claim 2, wherein the rotor includes at least one resilient ring member configured to apply the radially outward force to the respective vanes.

5. The system according to claim 1, wherein the auxiliary vane pump comprises a pump housing having an inner surface around the at least one pumping chamber, the pump housing of the auxiliary vane pump including the irrigation inlet and outlet ports and the aspiration inlet and outlet ports of the auxiliary vane pump.

6. The system according to claim 1, wherein the auxiliary vane pump comprises a double pump housing including the at least one pumping chamber, wherein the at least one pumping chamber includes two pumping chambers, wherein the irrigation inlet and outlet ports of the auxiliary vane pump are coupled with a first one of the two pumping chambers and the aspiration inlet and outlet ports are coupled with a second one of the two pumping chambers.

7. The system according to claim 1, wherein the pump controller is configured:
   in response to an irrigation flow rate setting of X and an aspiration flow rate setting of Y, X being equal to Y, to operate the shared vane pump to simultaneously pump, at substantially the same flow rate of X, the irrigation fluid from the irrigation reservoir to the distal end of the medical instrument through the first irrigation line and the irrigation channel and the aspirated matter from the distal end of the medical instrument through the aspiration channel and the first aspiration line to the collection receptacle, while the auxiliary vane pump is idle;
   in response to an irrigation flow rate setting of X and an aspiration flow rate setting of Y, X being greater than Y, which is non-zero, to operate the shared vane pump at a flow rate of Y and to operate the auxiliary vane pump to pump the irrigation fluid from the irrigation reservoir to the distal end of the medical instrument through the second irrigation line and through the irrigation channel at a flow rate of X minus Y;

in response to an irrigation flow rate setting of X and an aspiration flow rate setting of Y, Y being greater than X, which is non-zero, to operate the shared vane pump at a flow rate of X and to operate the auxiliary vane pump to pump the aspirated matter from the distal end of the medical instrument through the aspiration channel and the second aspiration line to the collection receptacle at a flow rate of Y minus X;

in response to an irrigation flow rate setting of X and an aspiration flow rate setting of zero, to operate the auxiliary vane pump to pump, the irrigation fluid from the irrigation reservoir to the distal end of the medical instrument through the second irrigation line and the irrigation channel at a flow rate of X, while the shared vane pump is idle; and in response to an irrigation flow rate setting of zero and an aspiration flow rate setting of Y, to operate the auxiliary vane pump to pump, the aspirated matter from the distal end of the medical instrument through the aspiration channel and the second aspiration line to the collection receptacle at a flow rate of Y, while the shared vane pump is idle.

8. The system according to claim 7, further comprising:
an irrigation line valve disposed in the second irrigation line between the irrigation reservoir and the irrigation inlet of the auxiliary vane pump; and
an aspiration line valve disposed the second aspiration line between the aspiration channel of the medical instrument and the aspiration inlet of the auxiliary vane pump, and wherein
the pump controller is configured to selectively:
close the irrigation line valve and operate the auxiliary vane pump to pump the aspirated matter from the distal end of the medical instrument through the aspiration channel and the second aspiration line to the collection receptacle; and
close the aspiration line valve and operate the auxiliary vane pump to pump the irrigation fluid from the irrigation reservoir to the distal end of the medical instrument through the second irrigation line and the irrigation channel.

9. The system according to claim 1, wherein the medical instrument includes a phacoemulsification probe.

10. A medical method comprising:
coupling an irrigation channel and an aspiration channel of a medical instrument, which is configured to be inserted into a body part of a living subject, with an irrigation outlet port and an aspiration inlet port of a shared vane pump, respectively, and with an irrigation outlet port and an aspiration inlet port of an auxiliary vane pump, respectively, the irrigation channel and an aspiration channel being configured to carry irrigation fluid to a distal end of the medical instrument and remove aspirated matter from the distal end of the medical instrument, respectively;
coupling an irrigation reservoir, which is configured to store the irrigation fluid, with an irrigation inlet port of the shared vane pump via a first irrigation line;
coupling the irrigation reservoir with an irrigation inlet port of the auxiliary vane pump via a second irrigation line;
coupling a collection receptacle, which is configured to collect the aspirated matter, with an aspiration outlet port of the shared vane pump via a first aspiration line, the irrigation inlet and outlet ports and the aspiration inlet and outlet ports being coupled with a pumping chamber of the shared vane pump;
coupling the collection receptacle with an aspiration outlet port of an auxiliary vane pump via a second aspiration line, the aspiration outlet port of the auxiliary vane pump being coupled with a pumping chamber of the auxiliary vane pump;
simultaneously pumping via the pumping chamber of the shared vane pump, at substantially the same flow rate, the irrigation fluid from the irrigation reservoir to the distal end of the medical instrument through the irrigation channel and the aspirated matter from the distal end of the medical instrument through the aspiration channel to the collection receptacle;
selectively pumping, via the pumping chamber of the auxiliary vane pump, the irrigation fluid from the irrigation reservoir to the distal end of the medical instrument through the second irrigation line and the irrigation channel, or the aspirated matter from the distal end of the medical instrument through the aspiration channel and the second aspiration line to the collection receptacle; and
controlling operation of the shared vane pump and the auxiliary vane pump.

11. The method according to claim 10, further comprising:
in response to an irrigation flow rate setting of X and an aspiration flow rate setting of Y, X being equal to Y, operating the shared vane pump to simultaneously pump, at substantially the same flow rate of X, the irrigation fluid from the irrigation reservoir to the distal end of the medical instrument through the first irrigation line and the irrigation channel and the aspirated matter from the distal end of the medical instrument through the aspiration channel and the first aspiration line to the collection receptacle, while the auxiliary vane pump is idle;
in response to an irrigation flow rate setting of X and an aspiration flow rate setting of Y, X being greater than Y, which is non-zero, operating the shared vane pump at a flow rate of Y and operating the auxiliary vane pump to pump the irrigation fluid from the irrigation reservoir to the distal end of the medical instrument through the second irrigation line and through the irrigation channel at a flow rate of X minus Y;
in response to an irrigation flow rate setting of X and an aspiration flow rate setting of Y, Y being greater than X, which is non-zero, operating the shared vane pump at a flow rate of X and operating the auxiliary vane pump to pump the aspirated matter from the distal end of the medical instrument through the aspiration channel and the second aspiration line to the collection receptacle at a flow rate of Y minus X;
in response to an irrigation flow rate setting of X and an aspiration flow rate setting of zero, operating the auxiliary vane pump to pump, the irrigation fluid from the irrigation reservoir to the distal end of the medical instrument through the second irrigation line and the irrigation channel at a flow rate of X, while the shared vane pump is idle; and
in response to an irrigation flow rate setting of zero and an aspiration flow rate setting of Y, operating the auxiliary vane pump to pump, the aspirated matter from the distal end of the medical instrument through the aspiration channel and the second aspiration line to the collection receptacle at a flow rate of Y, while the shared vane pump is idle.

12. The method according to claim 11, further comprising selectively:

closing an irrigation line valve disposed in the second irrigation line between the irrigation reservoir and the irrigation inlet of the auxiliary vane pump, and operating the auxiliary vane pump to pump the aspirated matter from the distal end of the medical instrument through the aspiration channel and the second aspiration line to the collection receptacle; and closing an aspiration line valve disposed in the second aspiration line between the aspiration channel of the medical instrument and the aspiration inlet of the auxiliary vane pump, and operating the auxiliary vane pump to pump the irrigation fluid from the irrigation reservoir to the distal end of the medical instrument through the second irrigation line and the irrigation channel.

* * * * *